United States Patent [19]

Chono et al.

[11] Patent Number: 4,537,757
[45] Date of Patent: Aug. 27, 1985

[54] CRYSTALLINE ALUMINOSILICATE AZ-1 AND A PROCESS FOR PRODUCING THE SAME

[75] Inventors: Masazumi Chono; Hiroshi Ishida, both of Kurashiki, Japan

[73] Assignee: Asahi Kasei Kogyo Kabushiki Kaisha, Osaka, Japan

[21] Appl. No.: 595,069

[22] Filed: Mar. 30, 1984

Related U.S. Application Data

[63] Continuation-in-part of Ser. No. 562,495, Dec. 16, 1983, abandoned.

[30] Foreign Application Priority Data

Dec. 30, 1982 [JP] Japan ................................ 57-228283
Apr. 30, 1983 [JP] Japan ................................ 58-77265

[51] Int. Cl.$^3$ ............................................. C01B 33/28
[52] U.S. Cl. ................................... 423/328; 423/329; 502/77
[58] Field of Search ................................ 423/326–333; 502/60, 62, 77; 260/448 C

[56] References Cited

U.S. PATENT DOCUMENTS

| | | | |
|---|---|---|---|
| 3,702,886 | 11/1972 | Argauer et al. | 423/328 |
| 3,709,979 | 1/1973 | Chu | 423/328 |
| 3,804,746 | 4/1974 | Chu | 208/111 |
| 4,002,698 | 1/1977 | Kaeding | 260/671 M |
| 4,060,568 | 11/1977 | Rodewald | 260/682 |
| 4,073,865 | 2/1978 | Flanigen et al. | 423/339 |
| 4,086,186 | 4/1978 | Rubin et al. | 252/430 |
| 4,086,287 | 4/1978 | Kaeding et al. | 260/671 R |
| 4,090,981 | 5/1978 | Rodewald | 252/455 Z |
| 4,094,921 | 6/1978 | Kaeding et al. | 260/671 |
| 4,100,219 | 7/1978 | Rodewald | 260/682 |
| 4,108,881 | 8/1978 | Rollmann et al. | 502/62 X |
| 4,127,616 | 11/1978 | Rodewald | 260/671 R |
| 4,145,315 | 3/1979 | Rodewald | 252/455 Z |
| 4,420,467 | 12/1983 | Whittam | 423/328 |

FOREIGN PATENT DOCUMENTS 0065401 11/1982 European Pat. Off. .
0077624 4/1983 European Pat. Off. .

OTHER PUBLICATIONS

Wu et al., "The Journal of Physical Chemistry" vol. 83, No. 21, 1979, pp. 2777–2781.

Primary Examiner—Edward J. Meros
Attorney, Agent, or Firm—Sprung Horn Kramer & Woods

[57] ABSTRACT

A novel crystalline aluminosilicate which exhibits a specific X-ray diffraction pattern having at least seven diffraction lines showing the following relative intensities at the positions of the following respective diffraction angle ($2\theta$):

| Diffraction angle ($2\theta$, deg) | Relative intensity |
|---|---|
| 7.8 ± 0.2 | 5–30 |
| 8.7 ± 0.2 | 90–100 |
| 8.9 ± 0.2 | 90–100 |
| 17.5 ± 0.2 | 5–30 |
| 17.7 ± 0.2 | 5–30 |
| 23.1 ± 0.2 | 30–80 |
| 23.3 ± 0.2 | 20–50 |

Such a crystalline aluminosilicate is produced by the mutual reaction of the components of a mixture of a silica source, an alumina source, a sodium source and water in the presence of 1,8-diamino-4-aminomethyloctane. The crystalline aluminosilicate thus prepared has an excellent catalytic activity and exhibits a specific adsorption behavior. The novel crystalline aluminosilicate according to the present invention may be advantageously used as a catalyst for producing a disubstituted benzene from a monosubstituted benzene or for producing a lower olefin from methanol and/or dimethyl ether and as an adsorbent.

11 Claims, 7 Drawing Figures

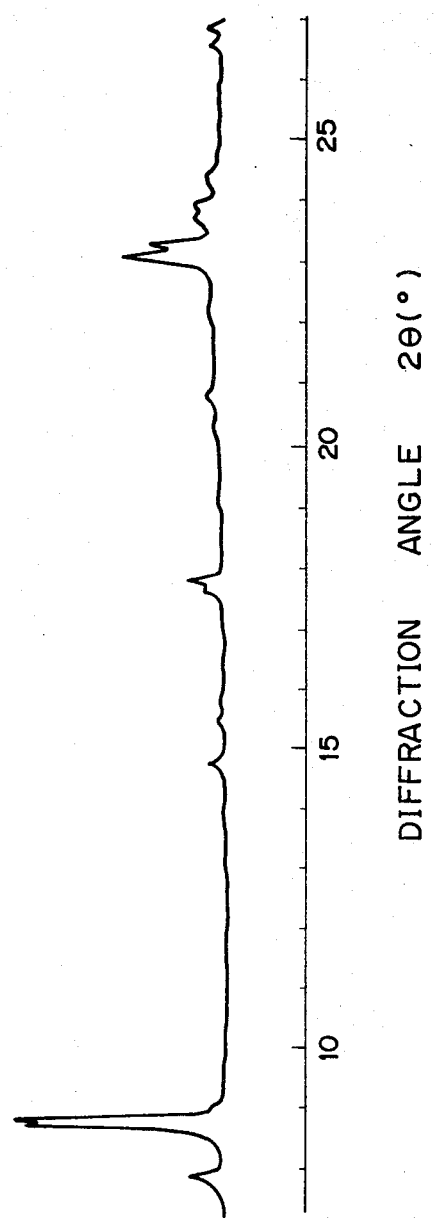

CRYSTALLINE ALUMINOSILICATE AZ-1 AND A PROCESS FOR PRODUCING THE SAME

This application is a continuation-in-part of our U.S. patent application Ser. No. 562,495 filed on Dec. 16, 1983, now abandoned.

This invention relates to a crystalline aluminosilicate. More particularly, the present invention is concerned with a novel crystalline aluminosilicate having a unique crystal form which shows a specific X-ray diffraction pattern different from those of conventional crystalline aluminosilicates. The present invention is also concerned with a process for producing the novel crystalline aluminosilicate. The crystalline aluminosilicate of the present invention is useful, especially as a catalyst for producing a 1,4-disubstituted benzene and for producing a lower olefin.

Crystalline aluminosilicates are substances generally known as zeolite and represented by the general formula $M_{2/n}O \cdot Al_2O_3 \cdot XSiO_2$ wherein M stands for at least one cation having a valence n and X is greater than or equal to 1. As is well known, the crystalline aluminosilicates have a rigid three-dimensional network of $SiO_4$ and $AlO_4$ in which the tetrahedra are cross-linked by the sharing of oxygen atoms whereby the ratio of the total aluminum and silicon atoms to oxygen is 1:2. The electrovalence of tetrahedra containing aluminum is balanced by the inclusion in the crystal of various cations. Both natural and synthetic aluminosilicates are commercially available and widely used as catalysts and adsorbents. Particularly, attention has been drawn to the use of crystalline aluminosilicates as a catalyst for production of a 1,4-disubstituted benzene from a monosubstituted benzene or for production of a lower olefin from a lower alcohol or a lower dialkyl ether. For example, paraxylene is very useful in manufacture of terephthalic acid which is an intermediate in the manufacture of synthetic fibers. Para-xylene may be produced using as a catalyst a crystalline aluminosilicate by disproportionation of toluene or by methylation of toluene. However, conventional crystalline aluminosilicates used as catalysts for producing a 1,4-disubstituted benzene are very poor in selectivity for the 1,4-disubstituted benzene, and the obtained reaction products contain a low concentration of 1,4-disubstituted benzene in the equilibrium mixture. Specifically, in the case of the production of para-ethyltoluene, the isomer distribution is 18.3% ortho-, 50.2% meta- and 31.5% para-ethylbenzene. Also in the case of the production of other 1,4-disubstituted benzenes, the proportions of 1,4-disubstituted benzenes in the obtained disubstituted benzenes are similar to that in the case of the production of para-ethylbenzene. As is well known, the isomers of 1,4-disubstituted benzenes have close boiling points. Therefore, difficulties are encountered to separate a 1,4-disubstituted benzene produced in a small amount from 1,2- and 1,3-isomers. Conventionally, the separation of such isomers has been effected by expensive superfraction and multistage refrigeration steps. Such process has involved high operation costs and has a limited yield.

Recently, a novel crystalline aluminosilicate (hereinafter referred to as "ZSM-5") has been developed and disclosed in U.S. Pat. No. 3,702,886. ZSM-5 is prepared by a hydrothermal synthetic reaction of a mixture of a silica source, an alumina source and an alkali metal source and water in the presence of a tetraalkylammonium ion. The thus prepared ZSM-5 is different in the crystal structure and properties from conventional zeolites, for example, faujasite zeolites (X and Y). Specifically, ZSM-5 possesses a novel crystal structure which shows a specific X-ray diffraction pattern as will be shown later, and are excellent in heat resistance and acid strength because of a high molar ratio of $SiO_2$ relative to $Al_2O_3$. The ZSM-5 having the above-mentioned characteristics has attracted attentions as a catalyst for the production of gasoline from methanol and for disproportionation, alkylation and isomerization of aromatic hydrocarbons. However, when ZSM-5 is used as a catalyst for disproportionation or for alkylation of aromatic hydrocarbons such as monosubstituted benzenes, a high selectivity for a 1,4-disubstituted benzene cannot be attained. In order to attain using as a catalyst ZSM-5 a high selectivity for a 1,4-disubstituted benzene, ZSM-5 should be subjected to a modifying treatment involving complicated steps before use as a catalyst. Specifically, ZSM-5 prepared by a hydrothermal reaction as mentioned before is subjected to calcination in the air, ion exchange with hydrogen ion, drying (or calcination), impregnation with a metal ion (phosphorus ion and/or magnesium ion) and then calcination in the air. Such a modifying treatment of ZSM-5 is disclosed in U.S. Pat. Nos. 4,002,698 and 4,086,287. Because of the necessity of the above-mentioned complicated steps for modification of ZSM-5, the method of producing a 1,4-disubstituted benzene using as a catalyst a modified ZSM-5 is not advantageous from the commercial point of view. For this reason, the development of a novel crystalline aluminosilicate catalyst having a high selectivity for a 1,4-disubstituted benzene without subjecting to any modifying treatment has been desired in the art.

In the meantime, lower olefins, i.e., ethylene, propylene and butene, are valuable hydrocarbons and constitute building blocks from which many other commercially useful products can be manufactured. With respect to the production of such valuable lower olefins, it is known that a certain zeolite is effective in converting lower alcohols or ethers to an olefin rich hydrocarbon mixture. Specifically, zeolites such as ZSM-34 as disclosed in U.S. Pat. No. 4,086,186 and erionite are effective as catalysts in selectively producing lower olefins from methanol and/or dimethyl ether. However, such catalysts rapidly lose their catalytic activities and, hence, are not advantageously used for the production of lower olefin on a commercial scale. Incidentally, ZSM-5 as mentioned before and ZSM-11 as disclosed in U.S. Pat. Nos. 3,709,979 and 3,804,746 are effective as a catalyst in obtaining an aromatic rich gasoline from methanol and/or dimethyl ether but ineffective in obtaining lower olefins from methanol and/or dimethyl ether.

The present inventors have made extensive and intensive studies with a view to developing a crystalline aluminosilicate which not only exhibits a high catalytic activity in the reaction for producing a 1,4-disubstituted benzene from a monosubstituted benzene and in the reaction for producing a lower olefin from methanol and/or dimethyl ether but also can maintain its high catalytic activity for a long period of time.

As a result, the present inventors have unexpectedly found that when the mutual reaction of the components of a mixture of a silica source, an alumina source, a sodium source and water is carried out in the presence of a specific amine, i.e., 1,8-diamino-4-aminomethyloctane under specific conditions, there can be obtained a novel crystalline aluminosilicate showing a specific X-ray diffraction pattern different from those of conventionally known crystalline aluminosilicates, which novel crystalline aluminosilicate has unique properties and is particularly effective as a catalyst in producing a 1,4-disubstituted benzene from a monosubstituted benzene and in producing a lower olefin from methanol and/or dimethyl ether. The present invention has been made based on such a novel finding.

Accordingly, it is an object of the present invention to provide a novel crystalline aluminosilicate which has an excellent catalystic activity in producing a 1,4-disubstituted benzene from a monosubstituted benzene and in producing a lower olefin from methanol and/or dimethyl ether.

It is another object of the present invention to provide a process for producing such a novel crystalline aluminosilicate.

It is a further object of the present invention to provide a catalyst for producing a 1,4-disubstituted benzene from a monosubstituted benzene or for producing a lower olefin from methanol and/or dimethyl ether which comprises a novel crystalline aluminosilicate of the kind described above.

The foregoing and other objects, features and advantages of the present invention will be apparent to those skilled in the art from the following detailed description and appended claims taken in connection with accompanying drawings in which:

FIG. 7 is an X-ray diffraction pattern of a further crystalline aluminosilicate according to the present invention.

Figure 1:
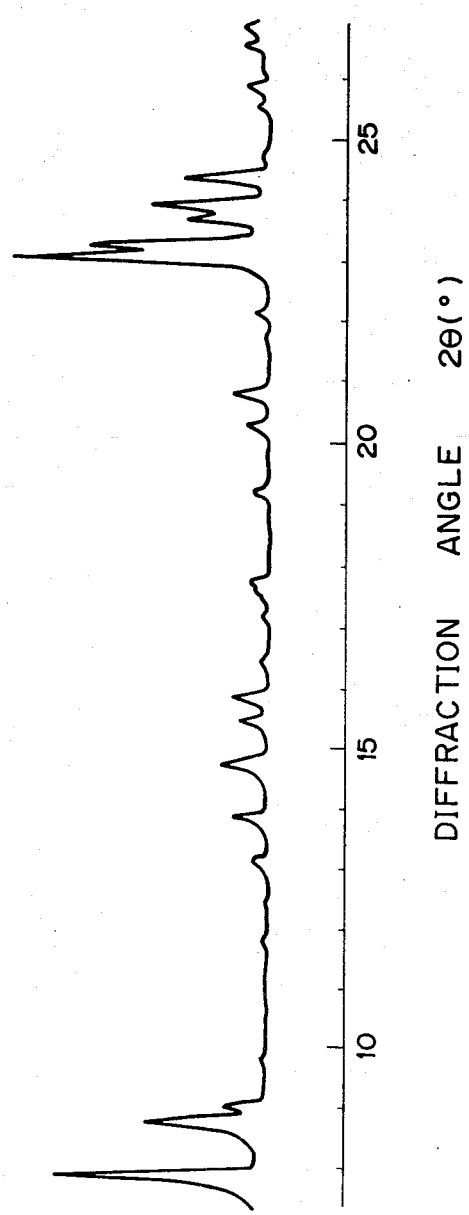
FIG. 1 is an X-ray diffraction pattern of ZSM-5 which is one of the conventional crystalline aluminosilicates.

In one aspect of the present invention, there is provided a crystalline aluminosilicate having a molar composition represented by the formula:

$M_{2/n}O \cdot Al_2O_3 \cdot YSiO_2$ 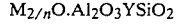

wherein M is at least one cation having a valence n and Y is at least 10, and having in its X-ray diffraction pattern obtained by using CuKα line at least seven diffraction lines showing the following relative intensities at the positions of the following respective diffraction angles (2θ):

| Diffraction angle (2θ, deg) | Relative intensity |
| --- | --- |
| 7.8 ± 0.2 | 5–30 |
| 8.7 ± 0.2 | 90–100 |
| 8.9 ± 0.2 | 90–100 |
| 17.5 ± 0.2 | 5–30 |
| 17.7 ± 0.2 | 5–30 |
| 23.1 ± 0.2 | 30–80 |
| 23.3 ± 0.2 | 20–50 | taking the intensity of the diffraction line at a diffraction angle of 8.7°±0.2° or 8.9°±0.2° as 100.

The present invention will now be described in detail.

The crystalline aluminosilicate according to the present invention (hereinafter often referred to as "AZ-1") is characterized by a specific X-ray diffraction pattern different from those of conventional crystalline aluminosilicates such as ZSM-5. Specifically, AZ-1 has in its X-ray diffraction pattern obtained by using CuKα line at least seven diffraction lines showing the following relative intensities at the positions of the following respective diffraction angles (2θ):

| Diffraction angle (2θ, deg) | Relative intensity |
| --- | --- |
| 7.8 ± 0.2 | 5–30 |
| 8.7 ± 0.2 | 90–100 |
| 8.9 ± 0.2 | 90–100 |
| 17.5 ± 0.2 | 5–30 |
| 17.7 ± 0.2 | 5–30 |
| 23.1 ± 0.2 | 30–80 |
| 23.3 ± 0.2 | 20–50 | taking the intensity of the diffraction line at a diffraction angle of 8.7°±0.2° or 8.9°±0.2° as 100. To obtain the X-ray diffraction pattern of a crystalline aluminosilicate, the X-ray diffractometry is conducted as follows. After completion of the reaction for producing a crystalline aluminosilicate, the resulting crystalline aluminosilicate is filtered off, washed with water, dried at 120° C. for 3 hours, calcined at 500° C. for 4 hours and allowed to stand at room temperature for at least 2 hours. The thus prepared sample is subjected to X-ray diffractometry. The X-ray diffraction pattern is obtained by using, for example, a recording X-ray diffractometer (GEIGERFLEX RAD-IIA manufactured and sold by Rigaku Corporation, Japan) and making measurements by the standard powder diffraction method using CuKα line. From the X-ray diffraction pattern, the above-mentioned X-ray diffraction characteristics can be easily obtained by observation and calculation.

Minor variation in the relative intensity occurs depending on the conditions in producing AZ-1 such as reaction time and molar composition of raw materials and depending on whether AZ-1 has been subjected to calcination treatment. But such variation is very small and the relative intensities of diffraction lines of AZ-1 are within the range as mentioned above. Further, in the X-ray diffraction pattern of AZ-1, said at least seven diffraction lines appearing at the positions of the above-mentioned specific diffraction angles are distinct from each other and there is no mixing of these diffraction lines, that is, any two adjacent diffraction lines do not mix with each other to assume a single diffraction line and, therefore, the number of diffraction lines will never be less than seven.

The difference between the X-ray diffraction pattern of ZSM-5 which is one of the conventional crystalline aluminosilicates and the X-ray diffraction pattern of AZ-1 will be apparent from the comparison of the relative intensities of the diffraction lines appearing at the respective diffraction angles, as will be explained below.

Figure 3:
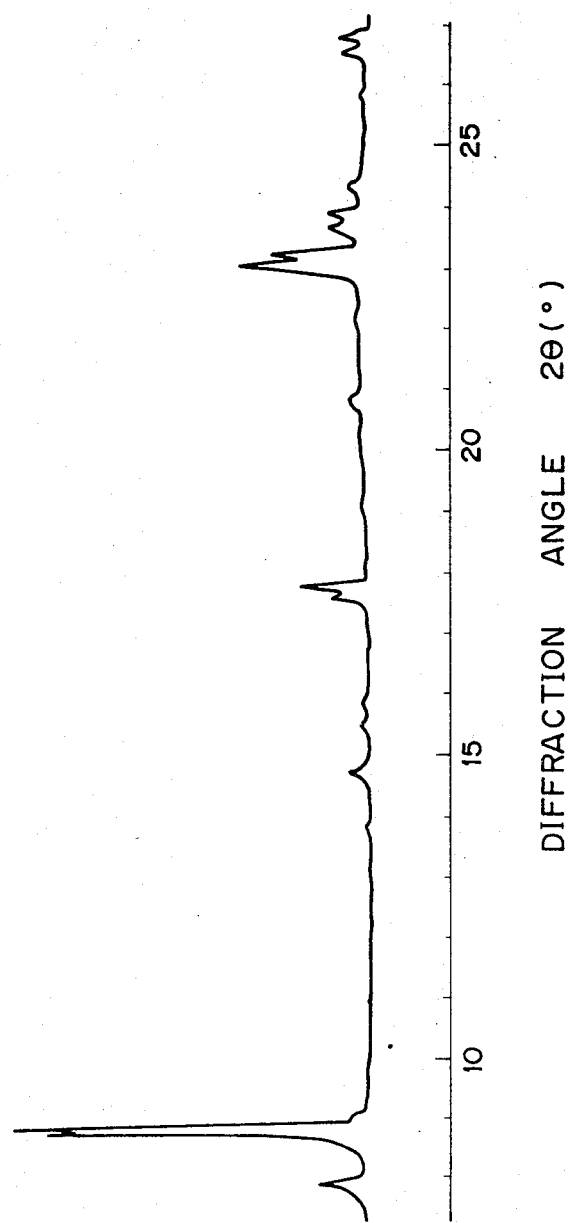
FIG. 3 is an X-ray diffraction pattern of a crystalline aluminosilicate according to the present invention.
Figure 4:
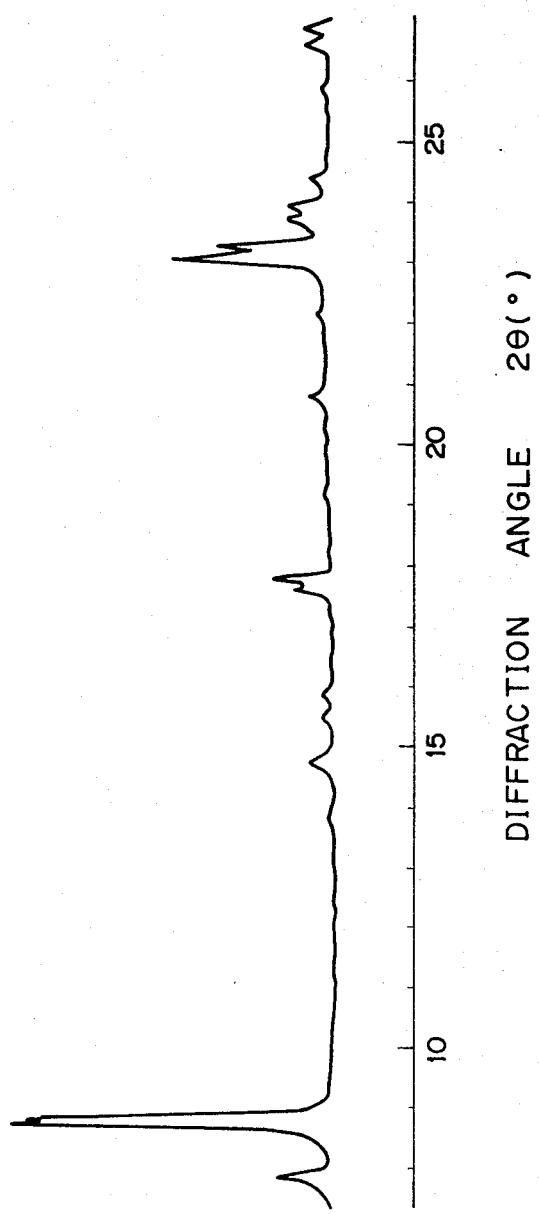
FIG. 4 is an X-ray diffraction pattern of another crystalline aluminosilicate according to the present invention.
Figure 6:
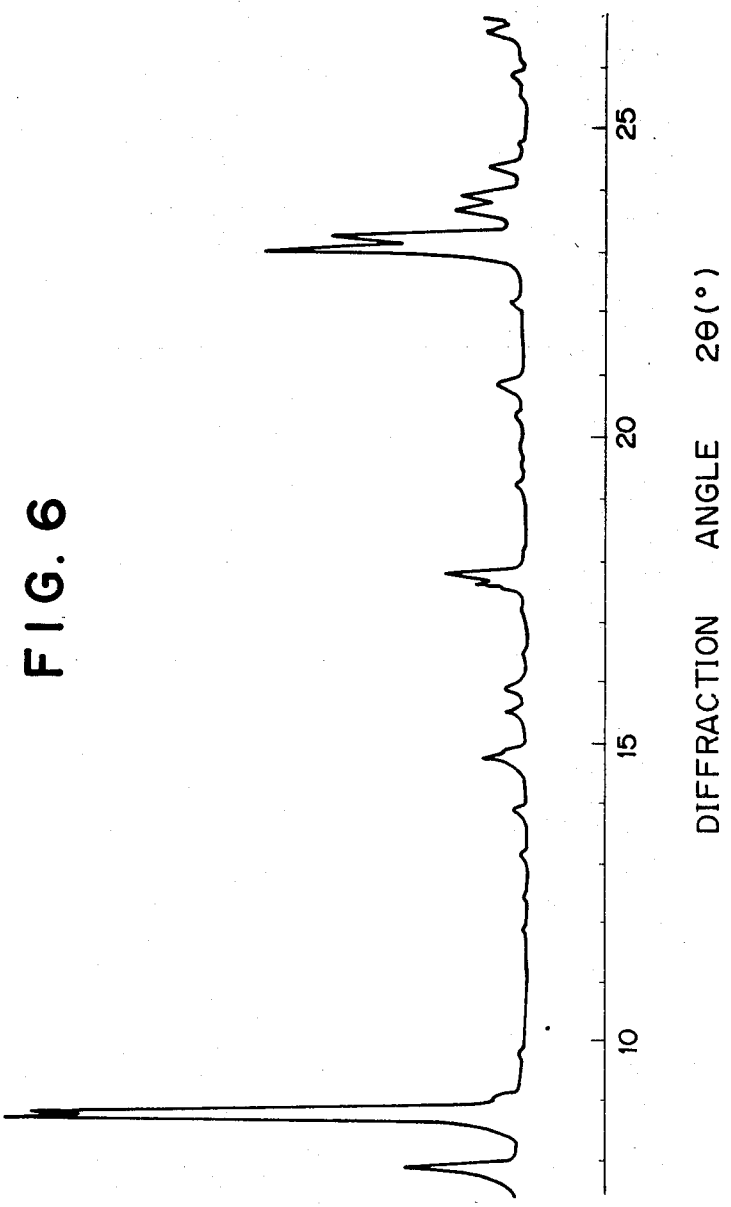
FIG. 6 is an X-ray diffraction pattern of still another crystalline aluminosilicate according to the present invention.

In FIG. 1, there is shown an X-ray diffraction pattern of ZSM-5 obtained in Comparative Example 1 which will be given later. In FIG. 3, there is shown an X-ray diffraction pattern of one form of AZ-1 obtained in Example 1 which will be given later. In FIG. 4, there is shown an X-ray diffraction pattern of another form of AZ-1 obtained in Example 2 which will be given later. In FIG. 6, there is shown an X-ray diffraction pattern of still another form of AZ-1 obtained in Example 3 which will be given later. In FIG. 7, there is shown an X-ray diffraction pattern of a further form of AZ-1 obtained in Example 4 which will be given later. The difference between the X-ray diffraction pattern of the conventional crystalline aluminosilicate ZSM-5 and that of AZ-1 is best illustrated in Table 1. In Table 1, the X-ray diffraction data for ZSM-5 which are obtained from FIG. 1 are compared with those for AZ-1 which are obtained from FIG. 4.

TABLE 1

| Diffraction angle 2θ(°) | Relative intensity | |
|---|---|---|
| | AZ-1 | ZSM-5 |
| 7.8 ± 0.2 | 21 | 82 |
| 8.7 ± 0.2 | 100 | 47 |
| 8.9 ± 0.2 | 97 | — |
| 17.5 ± 0.2 | 16 | 6 |
| 17.7 ± 0.2 | 22 | 7 |
| 23.1 ± 0.2 | 52 | 100 |
| 23.3 ± 0.2 | 39 | 71 |

As is apparent from Table 1, there are marked differences in the relative intensities of diffraction lines at the positions of the respective diffraction angle (2θ) between Az-1 and ZSM-5. Specifically, with respect to AZ-1, the X-ray diffraction line having the maximum intensity appears at 8.7° (2θ). On the other hand, with respect to ZSM-5, the X-ray diffraction line having the maximum intensity appears at 23.1°. When the ratio of the relative intensity at 8.7° to that at 23.1° is calculated with respect to AZ-1 and ZSM-5, it is noted that the ratio of the relative intensity at 8.7° to that at 23.1° with respect to AZ-1 is about 4 times that with respect to ZSM-5. The ratio of the relative intensity at 8.7° to that at 7.8° with respect to AZ-1 is also greatly different from that with respect to ZSM-5. The ratio of the relative intensity at 8.7° to that at 7.8° with respect to AZ-1 is about 4.8 as greatly different from about 0.6 with respect to ZSM-5. That is, the ratio of the relative intensity at 8.7° to that at 7.8° with respect to AZ-1 is about 8 times that with respect to ZSM-5. Further, AZ-1 according to the present invention exhibits a diffraction line having a very strong relative intensity at 8.7° and 8.9°. On the other hand, ZSM-5 exhibits a diffraction line having a medium relative intensity at 8.7° but has no diffraction line at 8.9°.

Figure 2:
FIG. 2 is a scanning electron photomicrograph (magnification: ×1,500) showing a crystal form of ZSM-5 of which the X-ray diffraction pattern is shown in FIG. 1.
Figure 5:
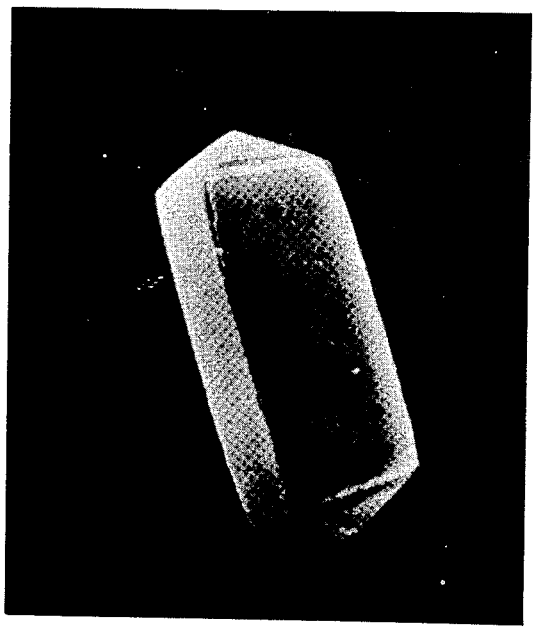
FIG. 5 is a scanning electron photomicrograph (magnification: ×1,500) showing a crystal form of a crystalline aluminosilicate according to the present invention, of which the X-ray diffraction pattern is shown in FIG. 4.

AZ-1 according to the present invention also has a unique crystal form which is different from that of the conventional crystalline aluminosilicate ZSM-5. This is illustratively shown in FIGS. 2 and 5. In FIG. 2, there is shown a scanning electron photomicrograph showing a crystal form of ZSM-5 obtained in Comparative Example 1 which will be given later. As can be seen from FIG. 2, the crystal of ZSM-5 is ordinarily in the shape of a sphere or an oval and/or an agglomerate thereof. In FIG. 5, there is shown a scanning electron photomicrograph showing a crystal form of AZ-1 obtained in Example 2 which will be given later. As can be seen from FIG. 5, the crystal of AZ-1 is ordinarily in the shape of a tetragonal column having a quadrangular pyramid at both ends thereof. In the crystal of AZ-1, the ratio of the length of its long axis (the top-to-top distance of the crystal to that of its short axis (the shortest of the axes which cross the long axis at a right angle thereto)) is usually 1.5 to 10. Moreover, the crystal of AZ-1 may exist not only in the form of a single crystal but also in the form of a polycrystal. In general, the particle size of AZ-1 is in the range of 0.05 to 200 μm. The specific crystal form of AZ-1 as explained above is not varied according to its particle size.

AZ-1 according to the present invention is greatly different in acidity also from ZSM-5.

AZ-1 obtained in Example 2 which will be given later and ZSM-5 obtained in Comparative Example 1 which will be given later were calcined at 325° C. for 2 hours in a helium atmosphere. 0.5 g of the calcined AZ-1 was packed into a glass tube. A predetermined amount of pyridine was intermittently passed through the glass tube using helium as a carrier to determine the amount of pyridine adsorbed on AZ-1. The amount of 4-methylquinoline adsorbed on AZ-1 was determined in the same manner as mentioned above, except that 4-methylquinoline was used instead of pyridine. Further, the amount of each of pyridine and 4-methylquinoline adsorbed on ZSM-5 was determined in the same manner as mentioned above, except that ZSM-5 was used instead of AZ-1. The results are shown in Table 2 below.

TABLE 2

| | A Adsorption of pyridine (μmol/g) | B Adsorption of 4-methyl-quinoline (μmol/g) | A/B Ratio of adsorption of pyridine to that of 4-methylquinoline |
|---|---|---|---|
| AZ-1 | 300 | 1.2 | 250 |
| ZSM-5 | 360 | 18.0 | 20 |

As is apparent from Table 2, AZ-1 is greatly different from ZSM-5 in ratio of adsorption of pyridine to that of 4-methylquinoline. The amount of pyridine adsorbed on a zeolite corresponds to the intra-pore acidity of the zeolite and the amount of 4-methylquinoline adsorbed on a zeolite corresponds to the extra-pore acidity of the zeolite. As can be seen from Table 2, AZ-1 is very high in ratio of adsorption of pyridine to that of 4-methylquinoline as compared with ZSM-5. This means that the proportion of the number of extra-pore acid sites to the number of intra-pore acid sites with respect to AZ-1 is very small as compared with that with respect to ZSM-5.

As is apparent from the foregoing, AZ-1 according to the present invention is quite different in its crystal form, X-ray diffraction pattern and adsorption behavior from the conventional zeolite ZSM-5.

AZ-1 according to the present invention is a zeolite having a high $SiO_2/Al_2O_3$ molar ratio of 10 or more, preferably 10 to 1000, more preferably 20 to 1000. Because of such a high silica content, AZ-1 is very excellent in thermal stability. The $SiO_2/Al_2O_3$ molar ratio may be determined according to conventional methods using a fluorescent X-ray analyzer.

In view of the specific crystal form, the high proportion of the number of extra-pore acid sites to the number of intra-pore acid sites and high thermal stability, AZ-1 according to the present invention is suitable for use as an adsorbent and a catalyst for various reactions. Particularly, AZ-1 of which the molar ratio of $SiO_2$ to $Al_2O_3$ is 30 to 300 is preferably used as a catalyst and an adsorbent. In this connection, where AZ-1 is intended to be used as an acid catalyst, the cation of AZ-1 is preferably hydrogen or hydrogen and sodium, provided that in case the cation is hydrogen and sodium the Na/Al atomic ratio of AZ-1 is up to 0.95, preferably up to 0.8.

AZ-1 prepared according to a process as will be mentioned later contains sodium as a cation and it can be used without subjecting to any treatment as an adsorbent or a catalyst for various reactions. Further, AZ-1 of the present invention includes the product resulting from calcination of the prepared AZ-1 and the product resulting from partial or entire ion exchange of sodium contained as a cation in AZ-1 with other cations. With respect to the cations to be used for ion exchange of sodium contained as a cation in AZ-1 and the method for ion exchange, an explanation will be given later.

The water content of AZ-1 depends on the conditions under which it has been dried after synthesis. Further, AZ-1 subjected to calcination has no water but the calcined AZ-1 absorbs water when it is allowed to stand in the air after calcination.

AZ-1 according to the present invention preferably has a constraint index of 1 to 15 and a surface area of 100 to 300 $m^2$/g. Such an AZ-1 is very useful as a catalyst as will be specifically explained later. With respect to a constraint index and a surface area of AZ-1, a detailed explanation will also be given later.

In another aspect of the present invention, there is provided a process for producing a crystalline aluminosilicate which comprises preparing a mixture of a silica source, an alumina source, a sodium source, water and 1,8-diamino-4-aminomethyloctane and having the following molar composition:

| | |
|---|---|
| $SiO_2/Al_2O_3$ | 10 to 1000 |
| $Na/SiO_2$ | 0.05 to 1.0 |
| $H_2O/SiO_2$ | 5 to 200 |
| 1,8-diamino-4-aminomethyloctane/$SiO_2$ | 0.1 to 10 | and reacting the components of said mixture with one another at a temperature of 100° to 250° C.

As the source of silica, there may be mentioned any silica source which is generally used for producing conventional crystalline aluminosilicates, for example, a powdered silica, an aqueous solution of sodium silicate, silica sol, etc. Among them, a silica sol is particularly preferably employed.

As an alumina source, there may be mentioned any material which is generally employed for producing conventional crystalline aluminosilicates, for example, a powdered alumina, aluminum sulfate, sodium aluminate and the like.

According to the present invention, the silica source is used in such an amount that the molar ratio of $SiO_2$ to $Al_2O_3$ is 10 to 1000, preferably 20 to 300. When the molar ratio of $SiO_2$ to $Al_2O_3$ is less than 10, the crystallization of an aluminosilicate does not take place. On the other hand, the upper limit of the molar ratio of $SiO_2$ to $Al_2O_3$ is not critical, but generally 1000.

As a sodium source, sodium hydroxide, sodium silicate and the like are generally used. Of them, particularly preferred is sodium hydroxide. The sodium source is used in such an amount that the $Na/SiO_2$ molar ratio is in the range of 0.05 to 1.0, preferably 0.05 to 0.5, more preferably 0.1 to 0.3.

When the $Na/SiO_2$ molar ratio is less than 0.05, the crystallization of an aluminosilicate does not take place. On the other hand, the $Na/SiO_2$ molar ratio is more than 1.0, ZSM-5 which is one of the conventional zeolites is obtained but AZ-1 cannot be obtained.

According to the present invention, it is requisite that the hydrothermal reaction for producing a crystalline aluminosilicate of the present invention be carried out in the presence of 1,8-diamino-4-aminomethyloctane represented by the formula:

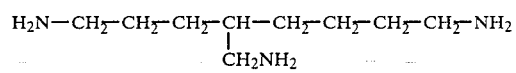

1,8-diamo-4-aminomethyloctane is a known compound and generally obtained by the hydrogeneration of 1,3,6-tricyanohexane in the presence of a hydrogeneration catalyst such as a Raney catalyst, a catalyst composed of nickel on silica, silica-alumina or the like, a platinum catalyst or a palladium/carbon catalyst, or a reducing agent such as $LiAlH_4$ [U.S. Pat. No. 3,246,000 and J. Org. Chem., 30 (5) 1351 (1965)]. Further, 1,8-diamino-4-aminomethyloctane may be obtained by the hydrogeneration of 1,3,6-tricyanohexane in the liquid phase using a Raney cobalt as a catalyst and water as a promotor (Japanese Patent Application Publication No. 57-55705/1982). 1,3,6-tricyanohexane which is a raw material of 1,8-diamino-4-aminomethyloctane may be prepared by the electrolytic reduction of acrylonitrile or by the reduction of acrylonitrile using sodium amalgam [J. Org. Chem., 30 (5) 1351 (1965) and Japanese Patent Application Publication No. 45-31179/1970].

1,8-diamino-4-aminomethyloctane is used in such an amount that the molar ratio of 1,8-diamino-4-aminomethyloctane to $SiO_2$ is 0.1 to 10, preferably 0.5 to 3. Where the molar ratio of 1,8-diamino-4-aminomethyloctane to $SiO_2$ is less than 0.1, AZ-1 cannot be obtained but other aluminosilicate than AZ-1 is prepared. On the other hand, where the molar ratio of 1,8-diamino-4-aminomethyloctane to $SiO_2$ is more than 10, AZ-1 cannot be obtained but the conventional zeolite ZSM-5 is formed.

In the present invention, the production of AZ-1 should be carried out in the presence of water. Water is used in such an amount that the molar ratio of water to $SiO_2$ is 5 to 200, preferably 10 to 50. In case the molar ratio of water to $SiO_2$ is less than 5, the crystallization of an aluminosilicate does not take place. On the other hand, in case the molar ratio of water to $SiO_2$ is more than 200, AZ-1 cannot be obtained in high yield.

According to the present invention, a silica source, an alumina source, a sodium source, water and 1,8-diamino-4-aminomethyloctane are mixed in molar ratios as mentioned above to prepare a mixture. It is preferred that the pH value of the thus obtained mixture be adjusted to 10 to 13, more preferably 11.5 to 12.5 by adding an acid such as sulfuric acid. The mixture of raw materials is then heated at a temperature of 100° to 250° C., preferably 120° to 200° C., thereby to effect the mutual reaction of the raw materials. When the reaction temperature is less than 100° C., the crystallization of an aluminosilicate does not take place. On the other hand, when the reaction temperature is higher than 250° C., the yield of AZ-1 is poor since aluminosilicates other than AZ-1 are produced. The pressure is performing the reaction is not critical. But the reaction is generally carried out under atmospheric pressure or autogenetic pressure. The reaction time is also not critical, and the reaction is carried out for a time sufficient to attain the growth of crystals of the aluminosilicate. Therefore, the reaction time may vary depending upon the reaction temperature and the molar ratios of raw materials, but is generally 5 to 200 hours.

In practicing the process of the present invention, it is preferable to perform a high speed agitation of a mixture of raw materials prior to the reaction of the mixture. Such a high speed agitation may be effected using a mixer such as a homogenizer or a high-speed rotary mixer. In this connection, it is preferred that the high speed agitation of the raw materials be effected at a linear speed of 1 to 10 m/sec (at the blade tip of the mixer).

The obtained crystalline aluminosilicate is separated from the reaction mixture by the conventional methods, for example, by cooling the whole to room temperature, filtering and water-washing. The crystalline product AZ-1 is thereafter dried at 100° to 200° C. for 2 to 24 hours.

The thus prepared AZ-1 generally contains as cation sodium, an organic cation derived from 1,8-diamino-4-aminomethyloctane and hydrogen. AZ-1 containing sodium as a cation may be used without subjecting to any treatment as an adsorbent or a catalyst for various reactions. According to need, the obtained AZ-1 may be calcined, for example, at 300° to 700° C. and the resultant may be used as an adsorbent or a catalyst. By calcination of AZ-1, most of the organic cation derived from 1,8-diamino-4-aminomethyloctane contained in AZ-1 is converted to hydrogen ion.

Further, sodium contained as a cation in AZ-1 may be partially or entirely ion-exchanged with other cations. As such cations, there may be mentioned hydrogen, transition metals such as Fe and Cu, noble metals such as Pt and Pd, alkali metals such as Li and K, and the like. The ion exchange may be effected according to the conventional methods. For example, to replace the sodium contained in AZ-1 by hydrogen, the ion exchange may be carried out by slurrying AZ-1 with an aqueous solution of a mineral acid such as hydrochloric acid. To replace the sodium contained in AZ-1 by a metal cation other than sodium, the ion exchange may be carried out by slurrying AZ-1 with an aqueous solution of any water soluble salts containing the metal cation.

In accordance with still another aspect of the present invention, there is provided a catalyst for producing a 1,4-disubstituted benzene from a monosubstituted benzene or for producing a lower olefin from methanol and/or dimethyl ether which comprises a crystalline aluminosilicate having a molar composition represented by the formula:

$$M_{2/n}O \cdot Al_2O_3 \cdot YSiO_2$$

wherein M is at least one cation having a valence n and Y is at least 10, and having in its X-ray diffraction pattern obtained by using CuK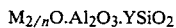α line at least seven diffraction lines showing the following relative intensities at the positions of the following respective diffraction angles (2θ):

| Diffraction angle (2θ, deg) | Relative intensity |
|---|---|
| 7.8 ± 0.2 | 5–30 |
| 8.7 ± 0.2 | 90–100 |
| 8.9 ± 0.2 | 90–100 |
| 17.5 ± 0.2 | 5–30 |
| 17.7 ± 0.2 | 5–30 |
| 23.1 ± 0.2 | 30–80 |
| 23.3 ± 0.2 | 20–50 | taking the intensity of the diffraction line at a diffraction angle of 8.7°±0.2° or 8.9°±0.2° as 100.

The catalyst of the present invention comprises a novel aluminosilicate (AZ-1) as described above, and is one for producing a 1,4-disubstituted benzene from a monosubstituted benzene or for producing a lower olefin from methanol and/or dimethyl ether.

When the catalyst of the present invention is one for producing a 1,4-disubstituted benzene from a monosubstituted benzene, it is preferred that the monosubstituted benzene be a compound selected from the group consisting of monoalkyl benzenes of which the alkyl group has up to 3 carbon atoms, chlorobenzene, bromobenzene and iodobenzene. Further, the catalyst of the present invention is preferably used for producing a 1,4-disubstituted benzene which has an alkyl group having up to 3 carbon atoms at at least one of the 1- and 4-positions thereof. In this connection, it is more preferable that the alkyl group be methyl, ethyl or isopropyl group. As examples of 1,4-disubstituted benzenes to be produced using the catalyst of the present invention, there may be mentioned para-xylene, para-ethyltoluene, para-cymene, para-diethylbenzene, 1-ethyl-4-isopropylbenzene, para-diisopropylbenzene, 1-chloro-4-methylbenzene, 1-chloro-4-ethylbenzene, 1-chloro-4-isopropylbenzene, 1-bromo-4-methylbenzene, 1-bromo-4-ethylbenzene, 1-bromo-4-isopropylbenzene, 1-iodo-4-methylbenzene, 1-iodo-4-ethylbenzene and 1-iodo-4-isopropylbenzene. In the present invention, when the catalyst of the present invention is one for producing a 1,4-disubstituted benzene from a monosubstituted benzene, it is preferred that the catalyst comprise AZ-1 of which the cation is hydrogen and sodium, provided that the Na/Al atomic ratio is 0.05 to 0.95, preferably 0.1 to 0.8. The Na/Al atomic ratio of AZ-1 may be determined according to conventional methods using a fluorescent X-ray analyzer. By the use of the above-mentioned specific catalyst a 1,4-disubstituted benzene is produced with high selectivity. The above-mentioned specific AZ-1 may be prepared in various methods but is generally produced by calcination of AZ-1 as prepared in the aforementioned method at 300° to 700° C., preferably 400° to 600° C. for 2 to 24 hours. When the calcination temperature is lower than 300° C., the resulting catalyst is insufficient in its activity. On the other hand, when the calcination temperature is higher than 700° C., the crystal of AZ-1 tends to be degraded. In general, the conventional zeolites used as catalysts for producing a 1,4-disubstituted benzene by the alkylation or disproportionation of a monosubstituted benzene is subjected to ion exchange prior to use. By contrast, with respect to the catalyst of the present invention comprising AZ-1, a high selectivity for a 1,4-disubstituted benzene can be attained even when the catalyst of the present invention is not subjected to the ion exchange.

An extremely high selectivity for a 1,4-disubstituted benzene can be attained when there is used a catalyst of the present invention comprising AZ-1 of which the cation is hydrogen and sodium and of which the Na/Al atomic ratio is within the range as mentioned above, and which has a constraint index of 1 to 15 and a surface area of 100 to 300 m$^2$/g as measured according to the BET method using nitrogen.

The term "constraint index" as used herein is intended to mean the ratio of the cracking rate constants for n-hexane and 3-methylpentane. With respect to the constraint index, reference may be made to J. Catal., 67, 218 (1981). The constraint index is determined as follows.

A mixture of equal weight of n-hexane and 3-methylpentane (hereinafter often referred to as "hydrocarbon mixture") is diluted with helium to give a mole ratio of helium to the hydrocarbon mixture of 4:1 and is passed over a predetermined amount of a zeolite at a temperature ranging from 260° to 510° C. Then, the amounts of n-hexane and 3-methylpentane remaining unchanged are determined. The constraint index is calculated as follows.

$$\text{Constraint index} = \frac{\log(\text{fraction of n-hexane remaining})}{\log(\text{fraction of 3-methylpentane remaining})}$$

In determining the constraint index, it is necessary to control LHSV (liquid hourly space velocity) so that the overall conversion is 10 to 60%. Usually, the determination of constraint index is carried out at an LHSV of 0.05 to 1.0 hr$^{-1}$.

The constraint index is related to the size of pores of a zeolite. For example, in the case of a zeolite having a twelve-membered ring structure which has a large pore size, the constraint index is one or less. This is so because both n-hexane and 3-methylpentane enter the pores, so that the cracking rate of 3-methylpentane becomes higher than that of n-hexane. On the other hand, in the case of a zeolite having an eight-membered ring structure which has a small pore size, the constraint index is 30 or more because n-hexane molecules are preferentially introduced into the pores and cracked. A zeolite having a ten-membered ring structure such as ZSM-5 has a constraint index value intermediate the constraint indexes of the zeolite having an eight-membered structure and the zeolite having a twelve-membered structure. In this connection, it is to be noted that even in the case of the same kind of zeolite the constraint index may vary according to the temperatures employed for determination thereof. For example, when the constraint index of ZSM-5 is determined at temperatures as mentioned above, the obtained values vary within the range of 1 to 12 [J. Catal., 67,218(1981)]. Therefore, it seems that it is preferable that the constraint index be determined at a certain fixed temperature. But, in the case of a zeolite having a low activity, the determination at a high temperature is needed because the zeolite does not show activity at a low temperature. On the other hand, in the case of a zeolite having a high activity, the determination at a low temperature is needed because when the determination is carried out at a high temperature the overall conversion of n-hexane and 3-methylpentane exceeds 60%. As is apparent from the foregoing, the constraint indexes of the zeolites having different activities cannot be determined at a certain fixed temperature. But, when the constraint index is determined at temperatures ranging from 260° to 510° C. so that the overall conversion of n-hexane and 3-methylpentane is in the range of 10 to 60%, the constraint index of a zeolite varies but remains within a specific range according to the kind of zeolites. For example, the constraint index of a zeolite having a twelve-membered structure is always one or less and that of ZSM-5 is always in the range of 1 to 12.

As mentioned above, it is preferred that the catalyst of the present invention for producing a 1,4-disubstituted benzene comprise AZ-1 having a constraint index of 1 to 15. It is more preferable that the catalyst of the present invention comprise AZ-1 having a constraint index of 10 to 15 as determined at 315° C. The reason why a high selectivity for a 1,4-disubstituted benzene can be attained when the catalyst comprising AZ-1 having a constraint index range as mentioned above is not fully elucidated. But, one of the reasons is believed to reside in the relatively small pore size of AZ-1 even as compared with the pore size of ZSM-5 which is represented by the difference in constraint index between AZ-1 and ZSM-5.

AZ-1 having a constraint index of 1 to 15 can be produced by controlling the reaction temperature and the reaction time in producing AZ-1. In general, the lower the reaction temperature and the shorter the reaction time, the lower the constraint index of the resulting AZ-1.

As mentioned above, in the present invention, it is preferred that the catalyst of the present invention for producing a 1,4-disubstituted benzene comprise AZ-1 having a surface area of 100 to 300 m$^2$/g as determined according to the BET method using nitrogen. It is more preferable that the catalyst of the present invention comprise AZ-1 having a surface area of 100 to 250 m$^2$/g as determined according to the BET method using nitrogen.

The term "surface area as determined according to the BET method" as used herein is intended to mean a surface area determined by the multilayer adsorption isotherm method which was proposed by Brunauer, Emmett and Teller [JACS, 60, 309 (1938)]. This method is most generally employed for determining a surface area of a porous substance. The surface area of a zeolite as measured according to the BET method (hereinafter often referred to as "BET surface area") has a correlation with the crystallinity of the zeolite. Generally, AZ-1 having a high crystallinity has a BET surface area of about 350 to 400 m$^2$/g. But, when the catalyst of the present invention comprising AZ-1 having a relatively low crystallinity, i.e., 100 to 300 m$^2$/g is used for producing a 1,4-disubstituted benzene, a high selectivity for the 1,4-disubstituted benzene can be attained. Where the BET surface area of AZ-1 is less than 100 m$^2$/g, the catalyst comprising such an AZ-1 is high in selectivity for the 1,4-disubstituted benzene but is low in activity. On the other hand, where the BET surface area of AZ-1 is more than 300 m$^2$/g, the selectivity for a 1,4-disubstituted benzene of the catalyst such as AZ-1 is not sufficient and decreases according to the increase of the BET surface area.

The reason why the AZ-1 having a relatively low crystallinity shows a high selectivity for a 1,4-disubstituted benzene is not fully elucidated. However, it is presumed to be that the crystal of such an AZ-1 has a specific porous structure and a specific surface structure.

AZ-1 having a BET surface area of 100 to 300 m$^2$/g can be produced by controlling the reaction temperature and the reaction time in producing AZ-1. In general, the lower the reaction temperature and the shorter the reaction time, the lower the BET surface area of the resulting AZ-1.

When the catalyst of the present invention is one for producing a lower olefin from methanol and/or dimethyl ether, it is preferred that the catalyst of the present invention comprise AZ-1 of which the cation is hydrogen or hydrogen and sodium, provided that in case the cation is hydrogen and sodium the Na/Al atomic ratio is up to 0.7, preferably up to 0.5. The term "lower olefin" as used in the present invention is intended to mean olefins which are relatively small in the number of carbons, such as ethylene, propyrene and butene. The above-mentioned specific AZ-1 may be produced by various methods, for example, a method in which AZ-1 as prepared in the aforementioned method is calcined at a temperature of 300° to 700° C., preferably 400° to 600° C. for 2 to 24 hours or a method in which the cation of AZ-1 as prepared in the aforementioned method is partially or entirely ion exchanged with an acid in the method as mentioned above and then calcined at a temperature of 300° to 700° C., preferably 400° to 600° C. for 2 to 24 hours.

The conditions for producing a 1,4-disubstituted benzene from a monosubstituted benzene using as catalysts conventional zeolites can apply to the production of a 1,4-disubstituted benzene using the catalyst of the present invention, and the disproportionation of a monosubstituted benzene or the alkylation of a monosubstituted benzene is generally carried out at a temperature between about 300° C. and about 700° C. under atmospheric pressure or a pressure of 20 kg/cm$^2$G or less (U.S. Pat. Nos. 4,094,921, 4,100,219 and 4,090,981).

The conditions for producing a lower olefin from methanol and/or dimethyl ether using as catalysts conventional zeolites can also apply to the production of a lower olefin using the catalyst of the present invention, and the conversion of methanol and/or dimethyl ether to a lower olefin is generally carried out at a temperature between about 250° C. and about 450° C. under atmospheric pressure or a pressure of 10 kg/cm$^2$G or less (Japanese Patent Application Laid-Open Specification Nos. 56-135424/1981 and 57-59819/1982).

As described in the foregoing, a novel crystalline aluminosilicate (AZ-1) according to the present invention has a unique crystal form which shows a specific X-ray diffraction pattern different from those of conventional zeolites. AZ-1 can be used as a catalyst for various reactions and an adsorbent. The catalyst of the present invention comprising AZ-1 is useful not only for producing a 1,4-disubstituted benzene from a monosubstituted benzene but also for producing a lower olefin from methanol and/or dimethyl ether. Further, the catalyst of the present invention can maintain its high activity for a long period of time. In this connection, it should be emphasized that the catalyst of the present invention has a high selectivity for a 1,4-disubstituted benzene even when it is not subjected to any modifying treatment as opposed to conventional zeolites such as ZSM-5 in which a complicated modifying treatment, i.e., calcination→ion exchange→drying→impregnation→calcination, is needed before use as a catalyst.

The present invention will now be described in detail with reference to the following Examples that by no means limit the scope of the present invention.

In Examples, the X-ray diffraction patterns of crystalline aluminosilicate products were determined by using a recording X-ray diffractometer (GEIGERFLEX RAD-IIA manufactured and sold by Rigaku Corporation, Japan).

EXAMPLE 1

In 15 g of deionized water, there were dissolved 10 g of 1,8-diamino-4-aminomethyloctane, 0.5 g of aluminum sulfate hydrate [Al$_2$(SO$_4$)$_3$.18H$_2$O] and 0.5 g of sodium hydroxide to obtain an aqueous solution. Further, 20 g of a silica sol (SiO$_2$ content: 30% by weight) was added to the thus obtained aqueous solution so that a homogeneous aqueous solution was obtained. Then, 3.0 g of a 20% by weight aqueous solution of sulfuric acid was dropwise added to the homogeneous aqueous solution under agitation so that the pH value of the aqueous solution was adjusted to about 12, whereby a uniform gel was obtained. The resulting gel was put in a homogenizer, and kneaded for 10 minutes at a speed of 10,000 rpm (linear speed of the blade tip: 2 m/sec). The kneaded gel was put in a polytetrafluoroethylene-lined stainless steel autoclave and allowed to stand at 180° C. for 36 hours under autogenetic pressure to effect crystallization of the gel.

The crystallization product was filtered off, washed with water, dried at 120° C. for 3 hours and calcined at 500° C. for 4 hours. The resulting product was subjected to X-ray diffractometry to obtain an X-ray diffraction pattern as shown in FIG. 3. From the pattern, the product was identified as AZ-1. The following data were obtained with respect to the product AZ-1:

| | |
|---|---|
| SiO$_2$/Al$_2$O$_3$ in molar ratio | 60 |
| Na/Al in atomic ratio (By fluorescent X-ray analysis) | 0.4 |
| Constraint index at 315° C. | 15.0 |
| Surface area by the BET method using nitrogen | 240 m$^2$/g. |

EXAMPLE 2

In 200 g of deionized water, there were dissolved 50 g of 1,8-diamino-4-aminomethyloctane, 5 g of aluminum sulfate hydrate [Al$_2$(SO$_4$)$_3$.18H$_2$O] and 5 g of sodium hydroxide to obtain an aqueous solution. Further, 200 g of a silica sol (SiO$_2$ content: 30% by weight) was added to the thus obtained aqueous solution so that a homogeneous aqueous solution was obtained. Then, 30 g of a 20% by weight aqueous solution of sulfuric acid was dropwise added to the homogeneous aqueous solution under agitation so that the pH value of the aqueous solution was adjusted to about 12, whereby a uniform gel was obtained. The resulting gel was put in a homogenizer, and kneaded for 10 minutes at a speed of 10,000 rpm (linear speed of the blade tip: 2 m/sec). The kneaded gel was put in a polytetrafluoroethylene-lined stainless steel autoclave and allowed to stand at 180° C. for 150 hours under autogenetic pressure to effect crystallization of the gel.

The crystallization product was filtered off, washed with water, dried at 120° C. for 3 hours and calcined at 500° C. for 4 hours. The resulting product was subjected to X-ray diffractometry to obtain an X-ray diffraction pattern as shown in FIG. 4. From the pattern, the product was identified as AZ-1. Further, an electron photomicrograph of the product by a scanning-type electron microscope is given in FIG. 5. The figure shows that the product AZ-1 has a crystal form of a tetragonal column having quadrangular pyramids at both ends thereof.

The following data were obtained with respect to the product AZ-1:

| | |
|---|---|
| SiO$_2$/Al$_2$O$_3$ in molar ratio | 55 |
| Na/Al in atomic ratio (By fluorescent X-ray analysis) | 0.3 |
| Constraint index at 315° C. | 9.5 |
| Surface area by the BET method using nitrogen | 300 m$^2$/g. |

EXAMPLE 3

Substantially the same procedures as described in Example 2 were repeated except that the kneaded gel was allowed to stand at 200° C. for 69 hours under autogenetic pressure to effect crystallization of the gel.

The crystallization product was filtered off, washed with water, dried at 120° C. for 3 hours and calcined at 500° C. for 4 hours. The resulting product was subjected to X-ray diffractometry to obtain an X-ray diffraction pattern as shown in FIG. 6. From the pattern, the product was identified as AZ-1.

The following data were obtained with respect to the product AZ-1:

| | |
|---|---|
| SiO$_2$/Al$_2$O$_3$ in molar ratio | 70 |
| Na/Al in atomic ratio (By fluorescent X-ray analysis) | 0.2 |
| Constraint index at 315° C. | 9.0 |
| Surface area by the BET method using nitrogen | 400 m$^2$/g. |

EXAMPLE 4

In 600 g of deionized water, there were dissolved 500 g of 1,8-diamino-4-aminomethyloctane, 25 g of aluminum sulfate hydrate ]Al$_2$(SO$_4$)$_3$.18H$_2$O] and 25 g of sodium hydroxide to obtain an aqueous solution. Further, 1000 g of a silica sol (SiO$_2$ content: 30% by weight) was added to the thus obtained aqueous solution so that a homogeneous aqueous solution was obtained. Then, 150 g of a 20% by weight aqueous solution of sulfuric acid was dropwise added to the homogeneous aqueous solution under agitation so that the pH value of the aqueous solution was adjusted to about 12, whereby a uniform gel was obtained. The resulting gel was put in a homogenizer, and kneaded for 10 minutes at a speed of 12,000 rpm (linear speed of the blade tip: 2 m/sec). The kneaded gel was put in a polytetrafluoroethylene-lined stainless steel autoclave and allowed to stand at 130° C. for 100 hours under autogenetic pressure to effect crystallization of the gel.

The crystallization product was filtered off, washed with water, dried at 120° C. for 8 hours and calcined at 500° C. for 8 hours. The resulting product was subjected to X-ray diffractometry to obtain an X-ray diffraction pattern as shown in FIG. 7. From the pattern, the product was identified as AZ-1. The following data were obtained with respect to the product AZ-1:

| | |
|---|---|
| SiO$_2$/Al$_2$O$_3$ in molar ratio | 40 |
| Na/Al in atomic ratio (By fluorescent X-ray analysis) | 0.6 |
| Constraint index at 315° C. | 14.0 |
| Surface area by the BET method using nitrogen | 75 m$^2$/g. |

COMPARATIVE EXAMPLE 1

To 300 g of an aqueous solution of sodium silicate (containing 8.9% by weight of Na$_2$O, 28.9% by weight of SiO$_2$ and 62.2% by weight of H$_2$O), there were added 200 g of a 10% by weight aqueous solution of tetrapropylammonium hydroxide and then 105 g of a solution obtained by dissolving 5 g of aluminum nitrate hydrate [Al(NO$_3$)$_3$.9H$_2$O)] in 100 g of deionized water to obtain a homogeneous aqueous solution. The pH value of the homogeneous aqueous solution was adjusted to 10–10.5 by dropwise adding concentrated nitric acid while stirring to obtain a uniform gel. The gel was put in a polytetrafluoroethylene-lined stainless steel autoclave and allowed to crystallize while stirring at 180° C. for 24 hours under autogenetic pressure.

The crystallization product was filtered off, washed with water, dried at 120° C. for 3 hours and calcined at 500° C. for 4 hours. The resulting product was subjected to X-ray diffractometry to obtain an X-ray diffraction pattern as shown in FIG. 1. The thus obtained diffraction pattern was in agreement with that of the conventional crystalline aluminosilicate ZSM-5. Further, an electron photomicrograph of the product by a scanning-type electron microscope is given in FIG. 2. The figure shows that the product ZSM-5 consists of agglomerates of spherical or oval crystals.

With respect to the crystalline aluminosilicates of Examples 1 to 4 and Comparative Example 1, the relative intensities of the significant diffraction lines against varied diffraction angles are summarized in Table 3.

TABLE 3

| Diffraction angle 2θ(°) | Relative intensity | | | | |
|---|---|---|---|---|---|
| | Example 1 | Example 2 | Example 3 | Example 4 | Comparative Example 1 |
| 7.8 ± 0.2 | 16 | 21 | 24 | 23 | 82 |
| 8.7 ± 0.2 | 94 | 100 | 100 | 97 | 47 |
| 8.9 ± 0.2 | 100 | 97 | 94 | 100 | — |
| 17.5 ± 0.2 | 12 | 16 | 11 | 15 | 6 |
| 17.7 ± 0.2 | 22 | 22 | 17 | 22 | 7 |
| 23.1 ± 0.2 | 38 | 52 | 51 | 50 | 100 |
| 23.3 ± 0.2 | 30 | 39 | 39 | 38 | 71 |

EXAMPLE 5

Para-ethyltoluene was synthesized from toluene and ethylene using as a catalyst the AZ-1 obtained in Example 1, under the following experimental conditions:

| | |
|---|---|
| Amount of AZ-1 as catalyst | 5 g |
| Molar ratio of toluene to ethylene | 2.3 |
| WHSV (weight hourly space velocity) (on the basis of toluene) | 4 hr$^{-1}$ |
| Reaction temperature | 420° C. |
| Reaction pressure | Atmospheric |
| Apparatus | Fixed bed reactor |

The gaseous reaction products were led to a condenser and a receiver. The reaction products obtained between 2 hours after the beginning of the reaction and 3 hours after the beginning of the reaction were collected and analyzed by gas chromatography. The results are summarized below.

| | |
|---|---|
| Conversion of toluene | 22% |
| Yield of ethyltoluenes | 48% |

EXAMPLE 6

Para-ethyltoluene was synthesized from toluene and ethylene using as a catalyst the AZ-1 obtained in Example 1, under the following experimental conditions:

| | |
|---|---|
| Amount of AZ-1 as catalyst | 5 g |
| toluene/ethylene/H$_2$ in molar ratio | 6.6/1.0/2.0 |
| WHSV (weight hourly space velocity) (on the basis of toluene) | 6.0 hr$^{-1}$ |
| Reaction temperature | 420° C. |
| Reaction pressure | 5 kg/cm$^2$ |
| Apparatus | Fixed bed reactor |

The gaseous reaction products were led to a condenser and a receiver. The reaction products obtained between 20 hours after the beginning of the reaction and 22 hours after the beginning of the reaction were collected and analyzed by gas chromatography. The results are summarized below.

| | |
|---|---|
| Conversion of toluene | 14% |
| Yield of ethyltoluenes (based-on ethylene) | 91% |
| Para-ethyltoluene in ethyltoluenes | 95% |

EXAMPLE 7

Para-ethyltoluene was synthesized from toluene and ehtylene using as a catalyst the AZ-1 obtained in Example 2, under the same conditions as employed in Example 6. The gaseous reaction products were led to a condenser and a receiver. The reaction products obtained between 15 hours after the beginning of the reaction and 17 hours after the beginning of the reaction were collected and analyzed by gas chromatography. The results are summarized below.

| | |
|---|---|
| Conversion of toluene | 15% |
| Yield of ethyltoluenes (based on ethylene) | 94% |
| Para-ethyltoluene in ethyltoluenes | 75% |

EXAMPLE 8

Para-ethyltoluene was synthesized from toluene and ethylene using as a catalyst the AZ-1 obtained in Example 3, under the same conditions as employed in Example 6. The gaseous reaction products were led to a condenser and a receiver. The reaction products obtained between 20 hours after the beginning of the reaction and 22 hours after the beginning of the reaction were collected and analyzed by gas chromatography. The results are summarized below.

| | |
|---|---|
| Conversion of toluene | 15% |
| Yield of ethyltoluenes (based on ethylene) | 93% |
| Para-ethyltoluene in ethyltoluenes | 55% |

(based on ethylene)
Para-ethyltoluene in ethyltoluenes  93%

EXAMPLE 9

Para-ethyltoluene was synthesized from toluene and ethylene using as a catalyst the AZ-1 obtained in Example 4, under the same conditions as employed in Example 6. The gaseous reaction products were led to a condenser and a receiver. The reaction products obtained between 20 hours after the beginning of the reaction and 22 hours after the beginning of the reaction were collected and analyzed by gas chromatography. The results are summarized below.

| | |
|---|---|
| Conversion of toluene | 5.3% |
| Yield of ethyltoluenes (based on ethylene) | 34% |
| Para-ethyltoluene in ethyltoluenes | 99% |

COMPARATIVE EXAMPLE 2

Para-ethyltoluene was synthesized from toluene and ethylene using as a catalyst the ZSM-5 obtained in Comparative Example 1, under the same conditions as employed in Example 5. The gaseous reaction product were led to a condenser and a receiver. The reaction products obtained between 2 hours after the beginning of the reaction and 3 hours after the beginning of the reaction were collected and analyzed by gas chromatography. The results are summarized below.

| | |
|---|---|
| Conversion of toluene | 30% |
| Yield of ethyltoluenes (based on ethylene) | 60% |
| Para-ethyltoluene in ethyltoluenes | 30% |

EXAMPLE 10

Para-diethylbenzene was synthesized from ethylbenzene and ethylene using as a catalyst the AZ-1 obtained in Example 1, under the following experimental conditions:

| | |
|---|---|
| Amount of AZ-1 as catalyst | 5 g |
| Ethylbenzene/ethylene/H$_2$ molar ratio | 7/1/3 |
| WHSV (on the basis of ethylbenzene) | 6.0 hr$^{-1}$ |
| Reaction temperature | 350° C. |
| Reaction pressure | 2 kg/cm$^2$ |
| Apparatus | Fixed bed reactor. |

The gaseous reaction products were led to a condenser and a receiver. The reaction products obtained between 15 hours after the beginning of the reaction and 17 hours after the beginning of the reaction were collected and analyzed by gas chromatography. The results are summarized below.

| | |
|---|---|
| Conversion of ethylbenzene | 12% |
| Yield of diethylbenzenes (based on ethylene) | 78% |
| Para-diethylbenzene in diethylbenzenes | 96% |

EXAMPLE 11

Para-diethylbenzene was synthesized from ethylbenzene and ethylene using as a catalyst the AZ-1 obtained in Example 2, under the following experimental conditions:

| | |
|---|---|
| Amount of AZ-1 as catalyst | 5 g |
| Ethylbenzene/ethylene molar ratio | 2/1 |
| WHSV (on the basis of ethylbenzene) | 4 hr$^{-1}$ |
| Reaction temperature | 360° C. |
| Reaction Pressure | Atmospheric |
| Apparatus | Fixed bed reactor. |

The gaseous reaction product were led to a condenser and a receiver. The reaction products obtained between 2 hours after the beginning of the reaction and 3 hours after the beginning of the reaction were collected and analyzed by gas chromatography. The results are summarized below.

| | |
|---|---|
| Conversion of ethylbenzene | 33% |
| Yield of diethylbenzenes (based on ethylene) | 57% |
| Para-diethylbenzene in ethylbenzenes | 80% |

EXAMPLE 12

Para-xylene was synthesized from toluene and methanol using the AZ-1 obtained in Example 1, under the following experimental conditions:

| | |
|---|---|
| Amount of AZ-1 as catalyst | 5 g |
| Toluene/methanol/N$_2$ molar ratio | 2/1/12 |
| WHSV (on the basis of toluene) | 4 hr$^{-1}$ |
| Reaction temperature | 500° C. |
| Reaction pressure | Atmospheric |
| Apparatus | Fixed bed reactor |

The gaseous reaction products were led to a condenser and a receiver. The reaction products obtained between 1 hour after the beginning of the reaction and 2 hours after the beginning of the reaction were collected and analyzed by gas chromatography. The results are summarized below.

| | |
|---|---|
| Conversion of toluene | 20% |
| Yield of xylenes (based on methanol) | 38% |
| Para-xylene in xylenes | 90% |

EXAMPLE 13

Para-cymene was synthesized from isopropylbenzene and methanol using as a catalyst the AZ-1 obtained in Example 3, under the following experimental conditions:

| | |
|---|---|
| Amount of AZ-1 as catalyst | 5 g |
| Isopropylbenzene/methanol/N$_2$ molar ratio | 2/1/10 |
| WHSV (on the basis of isopropylbenzene) | 3 hr$^{-1}$ |
| Reaction temperature | 400° C. |
| Reaction Pressure | Atmospheric |
| Apparatus | Fixed bed reactor. |

The gaseous reaction products were led to a condenser and a receiver. The reaction products obtained between 1 hour after the beginning of the reaction and 2 hours after the beginning of the reaction were collected and analyzed by gas chromatography. The results are summarized below.

| | |
|---|---|
| Conversion of isopropylbenzene | 15% |
| Yield of cymenes (based on methanol) | 16% |
| Para-cymene in cymenes | 93% |

EXAMPLE 14

Toluene was subjected to disproportionation reaction using as a catalyst the AZ-1 obtained in Example 1, under the following experimental conditions:

| | |
|---|---|
| Amount of AZ-1 as catalyst | 5 g |
| Molar ratio of N$_2$ to toluene | 4 |
| WHSV | 2.0 hr$^{-1}$ |
| Reaction temperature | 500° C. |
| Reaction Pressure | Atmospheric |
| Apparatus | Fixed bed reactor. |

The gaseous product were led to a condenser and a receiver. The products obtained between 2 hours after the beginning of the reaction and 3 hours after the beginning of the reaction was collected and analyzed by gas chromatography. The results are summarized below.

| | |
|---|---|
| Conversion of toluene | 48% |
| Selectivity for para-xylene | 78% |

Selectivity for para-xylene was determined as follows.

Selectivity for para-xylene (%) =

$$\frac{\text{mole number of produced para-xylene}}{(\text{mole number of consumed toluene}) \times \frac{1}{2}} \times 100$$

EXAMPLE 15

Toluene was subjected to disproportionation reaction using as a catalyst the AZ-1 obtained in Example 2, under the following experimental conditions:

| | |
|---|---|
| Amount of AZ-1 as catalyst | 5 g |
| Molar ratio of N$_2$ to toluene | 3 |
| WHSV | 2.0 hr$^{-1}$ |
| Reaction temperature | 550° C. |
| Reaction pressure | Atmospheric |
| Apparatus | Fixed bed reactor. |

The gaseous reaction product were led to a condenser and a receiver. The reaction products obtained between 2 hours after the beginning of the reaction and 3 hours after the beginning of the reaction were collected and analyzed by gas chromatography. The results are summarized below.

| | |
|---|---|
| Conversion of toluene | 48% |
| Selectivity for para-xylene | 93% |

Selectivity for para-xylene was determined in the same manner as in Example 14.

EXAMPLE 16

Para-ethylchlorobenzene was synthesized from chlorobenzene and ethylene using as a catalyst the AZ-1 obtained in Example 1, under the following experimental conditions:

| | |
|---|---|
| Amount of AZ-1 as catalyst | 5 g |
| Molar ratio of chlorobenzene to ethylene | 6.0 |
| WHSV (on the basis of chlorobenzene) | 4.0 hr$^{-1}$ |
| Reaction temperature | 400° C. |
| Reaction Pressure | Atmospheric |
| Apparatus | Fixed bed reactor. |

The gaseous reaction products were led to a condenser and a receiver. The reaction products obtained between 2 hours after the beginning of the reaction and 3 hours after the beginning of the reaction were collected and analyzed by gas chromatography. The results are summarized below.

| | |
|---|---|
| Conversion of chlorobenzene | 12% |
| Yield of ethylchlorobenzenes (based on ethylene) | 65% |
| Para-ethylchlorobenzene in ethylchlorobenzenes | 98% |

EXAMPLE 17

Para-ethylbromobenzene was synthesized from bromobenzene and ethylene using as a catalyst the AZ-1 obtained in Example 1, under the following experimental conditions:

| | |
|---|---|
| Amount of AZ-1 as catalyst | 5 g |
| Molar ratio of bromobenzene to ethylene | 4.0 |
| WHSV (on the basis of bromobenzene) | 8.0 hr$^{-1}$ |
| Reaction temperature | 420° C. |
| Reaction pressure | Atmospheric |
| Apparatus | Fixed bed reactor. |

The gaseous reaction product were led to a condenser and a receiver. The reaction products obtained between 2 hours after the beginning of the reaction and 3 hours after the beginning of the reaction were collected and analyzed by gas chromatography. The results are summarized below.

| | |
|---|---|
| Conversion of bromobenzene | 13% |
| Yield of ethylbromobenzenes (based on ethylene) | 47% |
| Para-ethylbromobenzene in ethylbromobenzenes | 98% |

EXAMPLE 18

Methanol was converted to olefins using as a catalyst the AZ-1 obtained in Example 2, under the following experimental conditions:

| | |
|---|---|
| Amount of AZ-1 as catalyst | 5 g |
| Methanol/N$_2$ molar ratio | 1/3 |
| SV (space velocity) | 3000 hr$^{-1}$ |
| Reaction temperature | 330° C. |
| Reaction pressure | Atmospheric |
| Apparatus | Fixed bed reactor. |

The analysis of the gaseous reaction products was carried out every 20 minutes by gas chromatography between 9 hours after the beginning of the reaction and 10 hours after the beginning of the reaction. The results are summarized below.

| | |
|---|---|
| Conversion of methanol (average) | 22% |
| Selectivity for hydrocarbons (average) | 90% |

Selectivity for hydrocarbons was determined as follows.

$$\text{Selectivity for hydrocarbons (\%)} = \frac{A - (2B + C + D)}{A} \times 100$$

wherein A is the mole number of consumed methanol, B the mole number of produced dimethyl ether, C the mole number of produced CO and D the mole number of produced CO$_2$.

The so-obtained hydrocarbons had the following product distribution:

TABLE 4

| i | Component | Product Distribution (%)* |
|---|---|---|
| 1 | Methane plus Ethane | 2 |
| 2 | Ethylene | 35 |
| 3 | Propylene | 25 |
| 4 | Butene | 12 |
| 5 | Propane plus Butane | 8 |
| 6 | C$_5^+$ aliphatics | 10 |
| 7 | Aromatics | 8 |

Note
*Product distribution (%) = $\dfrac{N_i \cdot C_i}{\sum\limits_{i=1 \text{ to } 7} N_i \cdot C_i} \times 100$ wherein N is the mole number of produced component i; and C the carbon number of produced component i;

EXAMPLE 19

The AZ-1 obtained in Example 3 was subjected to ion-exchange using 5% HCl for 5 hours. The ion-exchanged sample was then filtered off, washed with water, dried at 120° C. for 3 hours and calcined at 500° C. for 4 hours. The resultant had a Na/Al atomic ratio of 0. Using the so-treated sample as the catalyst, methanol was converted to olefins under the same experimental conditions as described in Example 19. The analysis of the gaseous reaction products was carried out every twenty minutes by gas chromatography between 9 hours after the beginning of the reaction and 10 hours after the beginning of the reaction. The results are summarized below.

| | |
|---|---|
| Conversion of methanol (average) | 100% |
| Selectivity for hydrocarbons (average) | 100% |

Selectivity for hydrocarbons was determined in the same manner as in Example 18. The so-obtained hydrocarbons had the following product distribution:

TABLE 5

| i | Component | Product Distribution (%)* |
|---|---|---|
| 1 | Methane plus Ethane | 2 |
| 2 | Ethylene | 28 |
| 3 | Propylene | 20 |
| 4 | Butene | 15 |

TABLE 5-continued

| i | Component | Product Distribution (%)* |
|---|---|---|
| 5 | Propane plus Butane | 9 |
| 6 | $C_5^+$ Aliphatics | 15 |
| 7 | Aromatics | 11 |

Note
*Product distribution was determined in the same manner as in Example 18.

EXAMPLE 20

Dimethyl ether was converted to olefins using as a catalyst the ion-exchanged AZ-1 obtained in Example 19 under the following experimental conditions:

| | |
|---|---|
| Amount of AZ-1 as catalyst | 5 g |
| Dimethyl ether/$N_2$ molar ratio | 1/3 |
| SV (space velocity) | 3500 hr$^{-1}$ |
| Reaction temperature | 330° C. |
| Reaction pressure | Atmospheric |
| Apparatus | Fixed bed reactor |

The analysis of the gaseous reaction products was carried out every twenty minutes by gas chromatography between 4 hours after the beginning of the reaction and 5 hours after the beginning of the reaction. The results are summarized below.

| | |
|---|---|
| Conversion of dimethyl ether (average) | 98% |
| Selectivity for hydrocarbons (average) | 96% |

Selectivity for hydrocarbons was determined as follows.

$$\text{Selectivity for hydrocarbons (\%)} = \frac{E - (C + D)}{E} \times 100$$

wherein E is the mole number of consumed dimethyl ether, C the mole number of produced CO and D the mole number of produced $CO_2$.

The so-obtained hydrocarbon product had the following product distribution:

TABLE 6

| i | Component | Product Distribution (%) |
|---|---|---|
| 1 | Methane plus Ethane | 1 |
| 2 | Ethylene | 30 |
| 3 | Propylene | 25 |
| 4 | Butene | 12 |
| 5 | Propane plus Butane | 7 |
| 6 | $C_5^+$ Aliphatics | 13 |
| 7 | Aromatics | 12 |

Note
*Product distribution was determined in the same manner as in Example 18

EXAMPLE 21

5 g of AZ-1 as obtained in the same manner as described in Example 3 slurried with 100 ml of an aqueous 1N ferric nitrate [Fe(NO$_3$)$_3$.7H$_2$O] solution and allowed to stand at room temperature for 24 hours to effect ion exchange of the cation of AZ-1 with Fe. The obtained product was filtered off, washed with water, dried at 120° C. for 3 hours and calcined at 500° C. for 4 hours. In substantially the same manner as mentioned above, AZ-1's were ion exchanged respectively with Cu, Pd, Li and K. 1N CuCl$_2$, 0.1N Pd(NO$_3$)$_2$, 1N LiCl and 1N KCl were used as sources of Cu, Pd, Li and K, respectively. The obtained products were subjected to X-ray diffractometry. Each of the above-obtained products exhibited the same X-ray diffraction pattern as that of AZ-1 obtained in Example 3.

What is claimed is:

1. A crystalline aluminosilicate having a molar composition represented by the formula:

$$M_{2/n}O.Al_2O_3.YSiO_2$$

wherein M is at least one cation having a valence n and Y is at least 10, and having in its X-ray diffraction pattern obtained by using CuKα line at least seven diffraction lines showing the following relative intensities at the positions of the following respective diffraction angles (2θ):

| Diffraction angle (2θ, deg) | Relative intensity |
|---|---|
| 7.8 ± 0.2 | 5–30 |
| 8.7 ± 0.2 | 90–100 |
| 8.9 ± 0.2 | 90–100 |
| 17.5 ± 0.2 | 5–30 |
| 17.7 ± 0.2 | 5–30 |
| 23.1 ± 0.2 | 30–80 |
| 23.3 ± 0.2 | 20–50 | taking the intensity of the diffraction line at a diffraction angle of 8.7°±0.2° or 8.9°±0.2° as 100.

2. A crystalline aluminosilicate according to claim 1, wherein M is hydrogen or hydrogen and sodium, provided that in case M is hydrogen and sodium the Na/Al atomic ratio is up to 0.95.

3. A crystalline aluminosilicate according to claim 2, which has a constraint index ranging from 1 to 15 and a surface area of 100 to 300 m$^2$/g as measured according to the BET method using nitrogen.

4. A process for producing a crystalline aluminosilicate according to claim 1 which comprises preparing a mixture of a silica source, an alumina source, a sodium source, water and 1,8-diamino-4-aminomethyloctane and having the following molar composition:

| | |
|---|---|
| SiO$_2$/Al$_2$O$_3$ | 10 to 1000 |
| Na/SiO$_2$ | 0.05 to 1.0 |
| H$_2$O/SiO$_2$ | 5 to 200 |
| 1,8-diamino-4-aminomethyloctane/SiO$_2$ | 0.1 to 10 | and reacting the components of said mixture with one another at a temperature of 100° to 250° C.

5. A process according to claim 4, wherein said silica source is a silica sol and said sodium source is sodium hydroxide.

6. A catalyst for producing a 1,4-disubstituted benzene from a monosubstituted benzene or for producing a lower olefin from methanol and/or dimethyl ether which comprises a crystalline aluminosilicate having a molar composition represented by the formula:

$$M_{2/n}O.Al_2O_3.YSiO_2$$

wherein M is at least one cation having a valence n and Y is at least 10, and having in its X-ray diffraction pattern obtained by using CuKα line at least seven diffraction lines showing the following relative intensities at the positions of the following respective diffraction angles (2θ):

| Diffraction angle (2θ, deg) | Relative intensity |
| --- | --- |
| 7.8 ± 0.2 | 5–30 |
| 8.7 ± 0.2 | 90–100 |
| 8.9 ± 0.2 | 90–100 |
| 17.5 ± 0.2 | 5–30 |
| 17.7 ± 0.2 | 5–30 |
| 23.1 ± 0.2 | 30–80 |
| 23.3 ± 0.2 | 20–50 | taking the intensity of the diffraction line at a diffraction angle of 8.7°±0.2° or 8.9°±0.2° as 100.

7. A catalyst according to claim 6, wherein in the case of the catalyst for producing 1,4-disubstituted benzene from a monosubstituted benzene, said monosubstituted benzene is a compound selected from the group consisting of monoalkylbenzenes of which the alkyl group has up to 3 carbon atoms, chlorobenzene, bromobenzene and iodobenzene.

8. A catalyst according to claim 7, wherein said 1,4-disubstituted benzene has an alkyl group having up to 3 carbon atoms at at least one of the 1- and 4-positions thereof.

9. A catalyst according to claim 8, wherein M is hydrogen and sodium, provided that the Na/Al atomic ratio is 0.05 to 0.95.

10. A catalyst according to claim 9, wherein said crystalline aluminosilicate has a constraint index ranging from 1 to 15 and a surface area of 100 to 300 m$^2$/g as measured according to the BET method using nitrogen.

11. A catalyst according to claim 6, wherein in the case of the catalyst for producing a lower olefin from methanol and/or dimethyl ether, M is hydrogen or hydrogen and sodium, provided that in case M is hydrogen and sodium the Na/Al atomic ratio is up to 0.7.

* * * * *